(12) United States Patent
Meischner et al.

(10) Patent No.: US 7,017,392 B2
(45) Date of Patent: Mar. 28, 2006

(54) SYSTEM FOR MONITORING DILUTION

(75) Inventors: Christopher R. Meischner, Washington, IL (US); Nermin Jelacic, Peterborough (GB); Anthony Jones, Chillicothe, IL (US); Timothy E. Delaney, Peoria, IL (US); Scott A. Butzin, East Peoria, IL (US); Thomas G Muir, Edwards, IL (US)

(73) Assignee: Caterpillar Inc, Peoria, IL (US)

( * ) Notice: Subject to any disclaimer, the term of this patent is extended or adjusted under 35 U.S.C. 154(b) by 52 days.

(21) Appl. No.: 10/705,332

(22) Filed: Nov. 10, 2003

(65) Prior Publication Data

US 2005/0097942 A1    May 12, 2005

(51) Int. Cl.
*G01N 11/00* (2006.01)
(52) U.S. Cl. ............. 73/53.01; 73/53.05; 73/61.41; 73/61.43; 73/61.48; 73/116; 73/119 R
(58) Field of Classification Search .............. 73/53.01, 73/53.05, 61.41, 61.43, 61.48, 40.7, 49.7, 73/47, 116, 119 R, 120; 436/56, 60
See application file for complete search history.

(56) References Cited

U.S. PATENT DOCUMENTS

| 4,004,453 | A | * | 1/1977 | Thyrum | 73/61.59 |
| 4,762,167 | A | * | 8/1988 | Dobson | 165/11.1 |
| 5,120,661 | A | * | 6/1992 | Baker et al. | 436/164 |
| 5,274,335 | A | * | 12/1993 | Wang et al. | 324/689 |
| 5,488,855 | A | * | 2/1996 | Carter et al. | 73/53.05 |
| 5,831,151 | A | * | 11/1998 | Ondrus et al. | 73/61.41 |
| 6,227,038 | B1 | * | 5/2001 | Blossfeld et al. | 73/49.7 |

* cited by examiner

*Primary Examiner*—Daniel S. Larkin
(74) *Attorney, Agent, or Firm*—Finnegan, Henderson, Farabow, Garrett & Dunner

(57) ABSTRACT

The system for monitoring dilution has a commodity being stored separately from a first fluid. The commodity has a predetermined distinguishing parameter (DP2) and the first fluid has a predetermined distinguishing parameter (DP1) being different from that of the predetermined distinguishing parameter (DP2) of the commodity. During operation of an apparatus the first fluid dilutes the commodity. A monitoring station has a device therein in which the predetermined distinguishing parameter (DP2) of the commodity is distinguished from the predetermined distinguishing parameter (DP1) of the first fluid. The monitoring station has at least one of a display monitor and a recording device.

20 Claims, 3 Drawing Sheets

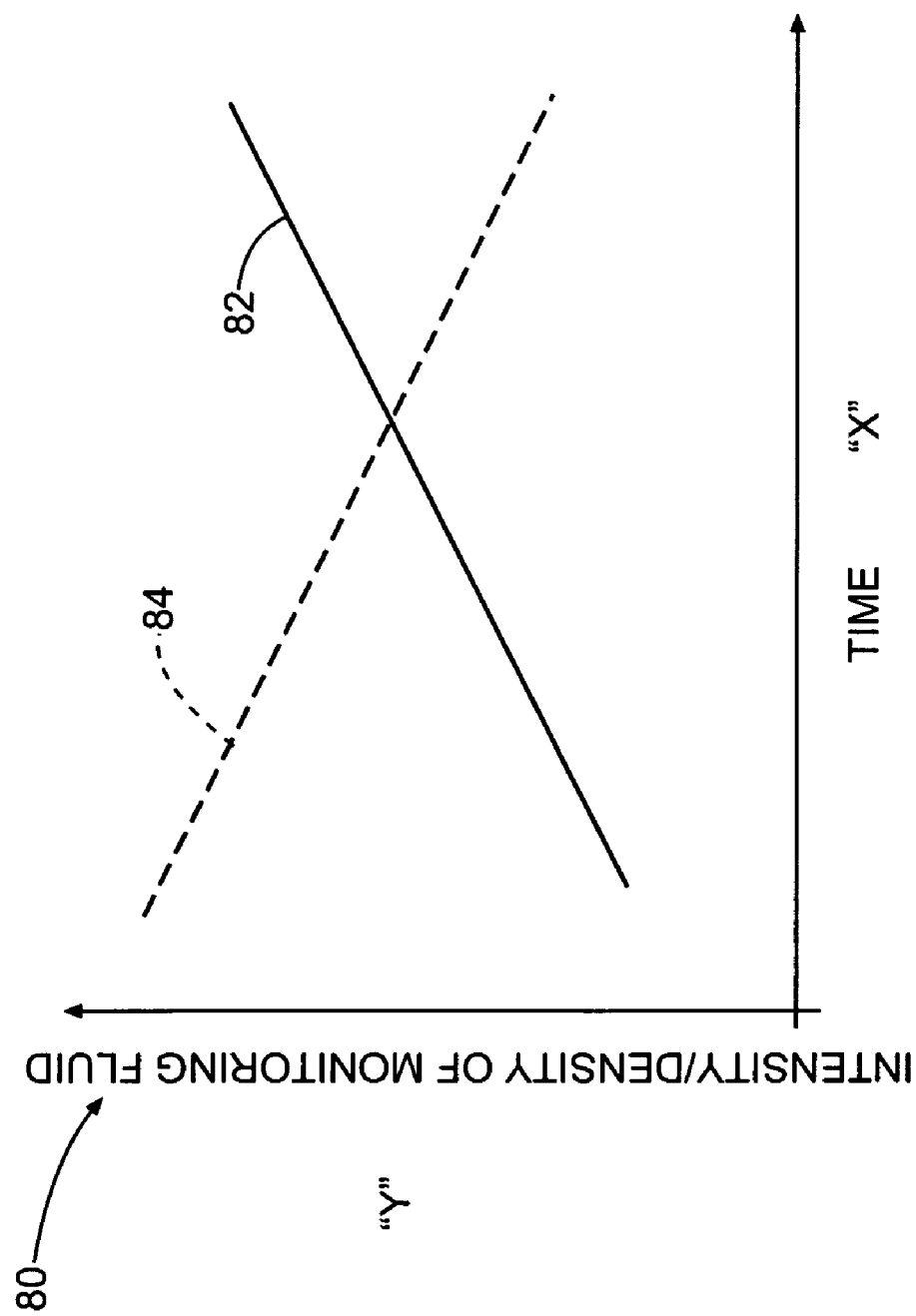

SYSTEM FOR MONITORING DILUTION

TECHNICAL FIELD

This invention relates to a system for monitoring a dilution and more particularly to monitoring the dilution of a first fluid to a second fluid.

BACKGROUND

The cleanliness of a fluid, in many applications, is essential to the operation and functionality of the fluid. In many applications, the cleanliness of the fluid determines the longevity of the operation. One such example, being a lubricating oil in an engine. As the engine operates, the lubricating oil becomes contaminated. Such contaminant being soot particles, iron, aluminum, cooper etc. Other contaminants being unburned fuel. As unburned fuel bypasses the rings the fuel is mixed with the lubricating oil. The ratio of fuel within the oil increases, thereby reducing the lubricating characteristics of the oil to a level which results in the oil film between moving parts breaking down and hence excess wear. In another example, the lubricating oil of the engine can be contaminated by a coolant, such as water or a mixture of water and antifreeze. Again, as the ratio of the contaminants, coolant, within the oil increases, the lubricating characteristics of the oil is reduced resulting in the longevity of the moving parts being reduced due to excess wear. Many contaminants, such as wear particles, are compensated for by changing the oil in a timely manner. However, some contaminants, such as unburned fuel and coolant are not necessarily predictable and thus, conventional oil changes may not compensate for such contaminants. Unburned fuel and coolant can very quickly deteriorate the functionality of lubricating oil causing increased wear particles. Thus, it is desirable to be able to monitor the contaminant level of fluids in an effective and timely manner. Thus, enabling the prediction of a rate of dilution of one fluid.

The present invention is directed to overcome one or more of the problems as set forth above.

SUMMARY OF THE INVENTION

In one embodiment of the invention a method of monitoring a diluting of a commodity is shown. The method comprises a commodity storage reservoir, the commodity has a predetermined distinguishing parameter (DP2). A first fluid storage reservoir has a first fluid therein, the first fluid has a predetermined distinguishing parameter (DP1) being different from the predetermined distinguishing parameter (DP2) of the commodity. An apparatus is connected to the first fluid storage reservoir and is connected to the commodity. And, a monitoring station is in operational communication with the commodity, the monitoring station has a device therein distinguishing between one of the predetermined distinguishing parameter (DP1) of the first fluid and the predetermined distinguishing parameter (DP2) of the commodity.

In another aspect of the invention, a system for monitoring a dilution of a first fluid into a second fluid of an apparatus is shown. The apparatus has a plurality of components and at least one of the components is movable relative to another one of the at least one of the components during a cycle of the apparatus. The system for monitoring a dilution comprises a first fluid which has a preestablished distinguishing parameter (DP1) and being stored in a first fluid storage reservoir. A second fluid has a preestablished distinguishing parameter (DP2) being different from the preestablished distinguishing parameter (DP1) of the first fluid and is stored in a second fluid storage reservoir. The first fluid storage reservoir is separated from the second fluid storage reservoir. A sealing member is interposed the first fluid and the second fluid, the sealing member is positioned on/in one of the plurality of components being movable relative to another one of the at least one of the components. A monitoring fluid is stored in one of the first fluid storage reservoir. The second fluid storage reservoir, the monitoring fluid has a preestablished distinguishing parameter (DP3) being different from the preestablished distinguishing parameter (DP1) of the first fluid and the preestablished distinguishing parameter (DP2) of the second fluid. And, a monitoring station is included in the system.

In another aspect of the invention a method for monitoring a dilution of a first fluid into a commodity of the system is shown. The method is comprised of having the commodity having a preestablished distinguishing parameter (DP2). Having a first fluid storage reservoir has the first fluid therein, the first fluid has a preestablished distinguishing parameter (DP1) being different from the preestablished distinguishing parameter (DP2) of the commodity. Having an apparatus being connected to the first fluid storage reservoir and being connected to the commodity. Having a monitoring station being operational communication with the commodity, the monitoring station having a device therein distinguishing between one of the predetermined distinguishing parameter (DP1) of the first fluid and the predetermined distinguishing parameter (DP2) of the commodity.

BRIEF DESCRIPTION OF THE DRAWINGS

FIG. 3 shows a pair of graphic representations of a diluting rate of the contaminating fluid to the operating fluid.

DETAILED DESCRIPTION

Figure 1:
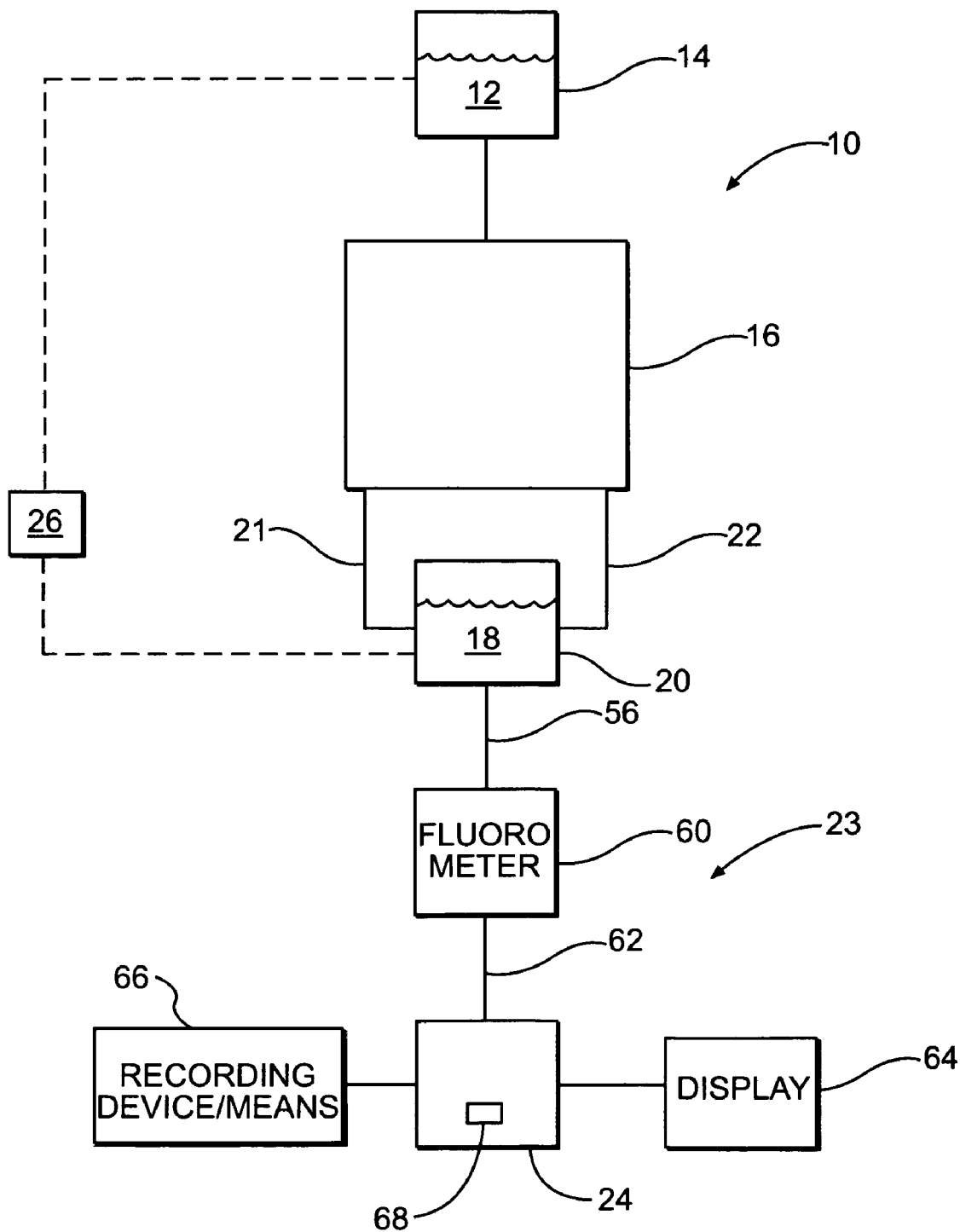
FIG. 1 is a schematic representation of a monitoring system.

A monitoring system or method or means 10 is shown in FIG. 1. The monitoring system has a contaminating fluid 12, first fluid, having a preestablished distinguishing parameter (DP1) or means for distinguishing a parameter which is stored in a fluid supply reservoir or means 14. An apparatus or means 16 has an operating fluid 18, a commodity or a second fluid, having a preestablished distinguishing parameter (DP2) or means for distinguishing a parameter being different from the preestablished distinguishing parameter (DP1) of the contaminating fluid 12 and is stored in a second fluid supply reservoir or means 20. The second fluid supply reservoir 20 may be a part or connected to the apparatus 16, or as shown in FIG. 1 be remotely connected to the apparatus 16 and have an inlet connection 21 and an outlet connection 22. A monitoring station or means 23 is in fluid communication with the operating fluid 18 and/or calibrated to the DP1 of the contaminating fluid 12, as is shown by the solid line and the phantom line respectively in FIG. 1. The monitoring station 23 distinguishes a dilution of one of the second fluid 18 into the first fluid 12 or the first fluid 12 into the second fluid 18 by monitoring a quantity of preestablished distinguishing parameter in one of the first fluid 12 or the second fluid 18.

In an alternative a monitoring fluid 26 is added to the system 10. The monitoring fluid 26 has a preestablished distinguishing parameter (DP3) or means for distinguishing a parameter. The preestablished distinguishing parameter (DP3) of the monitoring fluid 16 is different from each of preestablished distinguishing parameter (DP1) of the contaminating fluid 12 and the preestablished distinguishing parameter (DP2) of the operating fluid 18 and is functionally stored within either one of the first fluid supply reservoir 14 or the second fluid reservoir 20, as shown by dotted lines in FIG. 1. It is contemplated, that the distinguishing parameter of each of the contaminating fluid 12, the operating fluid 18 and the monitoring fluid 26 should not exist within each other. Or, if the distinguishing parameter does exist in two or each of the contaminating fluid 12, the operating fluid 18 and the monitoring fluid 26 the distinguishing parameter should be negligible or substantially non-measurable.

In other words, distinguishing parameter (DP) should be negligible or substantially non-measurable in all fluids. One does not want them to be the same in all fluids. Furthermore, if the distinguishing parameter is the same or near equal in at least two of the fluids it is not absolutely necessary that they be negligible or substantially non-measurable. The distinguishing parameter must be know and if necessary can be subtracted out as the background level, thus being predictable.

Figure 2:
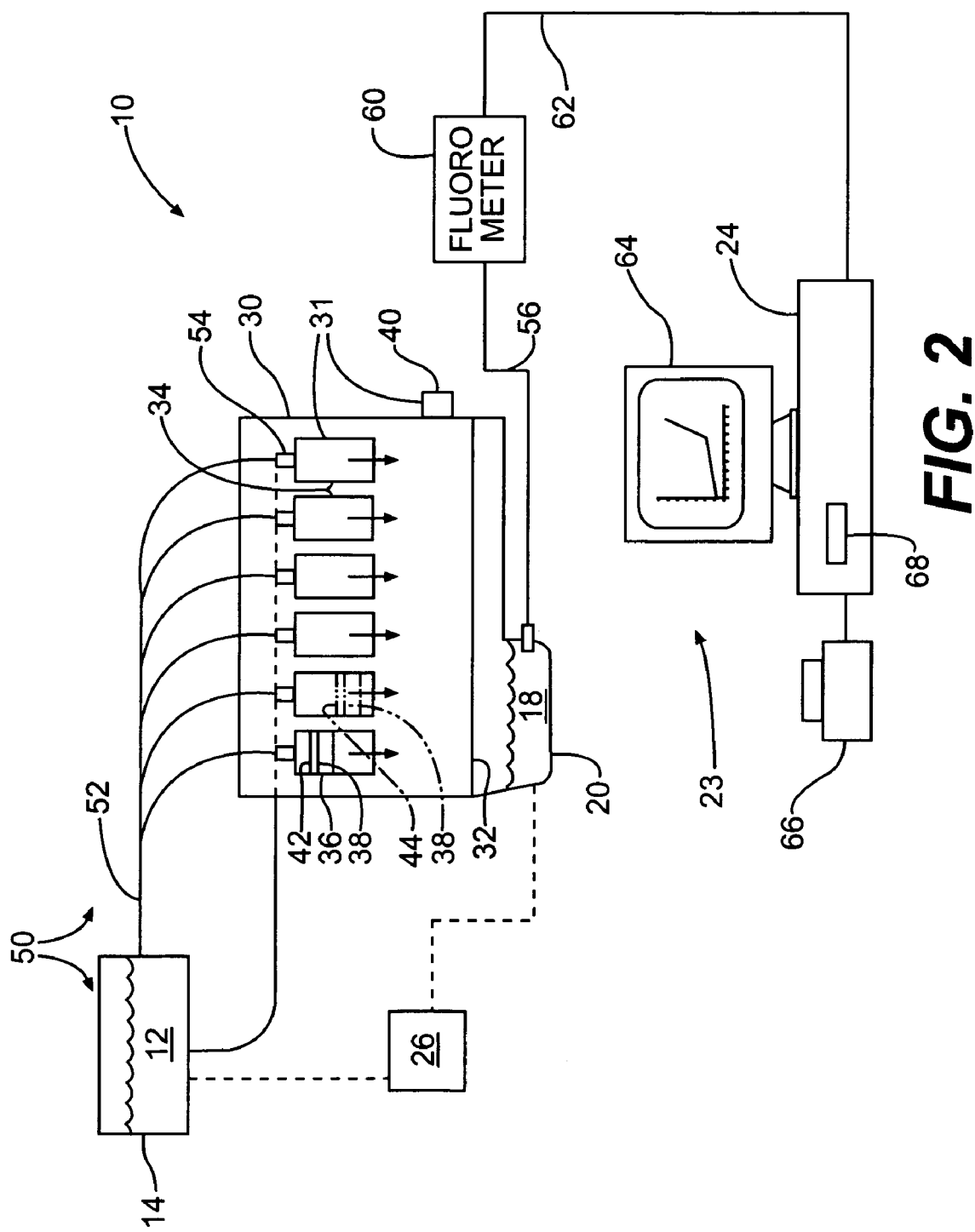
FIG. 2 is a monitoring system adapted for use with an engine.

As further shown in FIG. 2, the monitoring system 10 has been adapted for use with an engine 30 or another means. For example, the apparatus 16 of FIG. 1 is the engine 30. Other alternatives could be a cylinder such as used with a hydraulic system, or another system having an activation fluid, contaminating fluid 12, needing to be isolated from the operating fluid or commodity 18. The fluid supply reservoir, a fuel tank, 14 stores the contaminating fluid, which in this application is a fuel, 12 and to be more explicit is a diesel fuel 12. As an alternative, the contaminating fluid 12 can be either in a liquid form, a gaseous form or a solid form without changing the gist of the invention. Some examples of such being gasoline, natural gas, butane, coal, etc. The operating fluid, in this application, is a lubricating oil 18 and is stored in the operating fluid reservoir, an oil pan 20. The monitoring station 23 has a computer 24 or means and the monitoring fluid 26 is a fluorescent dye 26. In this application, the monitoring fluid, fluorescent dye 26 is in a solid form, powder. But, as an alternative, the monitoring fluid can be in any state, such as liquid or gas without changing the gist of the invention. The computer 24 in this application is a stationary unit, but as an alternative the monitoring station 23 could be a part of the engine 30 or a part of a machine, vehicle system, or any type of a system without changing the gest of the invention.

In other words, distinguishing parameter (DP) should be negligible or substantially non-measurable in all fluids. One does not want them to be the same in all fluids. Furthermore, if the distinguishing parameter is the same or near equal in at least two of the fluids it is not absolutely necessary that they be negligible or substantially non-measurable. The distinguishing parameter must be know and if necessary can be subtracted out as the background level, thus being predictable.

The engine 30 has a normal or preestablished operating cycle or cycles. The engine 30 is made up of a plurality of components 31. The engine 30 has a block 32 in which is positioned a plurality of cylinder bores 34. A piston 36 having a sealing member 38 thereon is operatively positioned in a respective one of the plurality of cylinder bores 34. As an alternative, the sealing member 38 can be placed on/in either of the piston 36, moving component, or the respective one of the plurality of cylinder bores 34, stationary component, without changing the gest of the invention. A crankshaft 40, partially shown in FIG. 2, is rotatably positioned in the block 32 in a conventional manner and functionally moves the piston 34 between a top position 42 and a bottom position 44. The bottom position 44 is shown in phantom in FIG. 2. The oil pan 20 is attached to the block 32 in a conventional manner. The oil pan 20 has a preestablished capacity. A fuel system 50 is operationally connected to the engine 30 in a conventional manner and has a supply line 52 in communication with the fluid supply reservoir or the fuel tank 14. The fuel tank 14 has a preestablished capacity. An injector 54 operatively supplies the diesel fuel 12 to a respective cylinder bore 32 during the movement of the piston 36 between the top position 42 and the bottom position 44.

In this application, a tube 56, being a fiber optic probe, is interposed the oil pan 20 and a flourometer 60 or means. And, a communication lead 62 or means is interposed the flourometer 60 and the computer 24. The computer 24 has a display monitor 64 or means and/or a recording device 66 or means operatively connected thereto. The computer 24 has a program 68 or means, represented by a disk, therein in which a preestablished grouping of distinguishing parameters (DP1, DP2, DP3) are established. In this application, the parameters (DP1, DP2, DP3) have a defined range of the ratio of the amount of diesel fuel 12, contaminating fluid, allowed to be in the lubricating oil 18, operating fluid. Other parameters such as a maximum ratio of the amount of contaminating fluid 12 to the operating fluid 18, or a minimum ratio of the amount of contaminating fluid 12 to the operating fluid 18 can be incorporated in the program 68 without changing the gist of the invention.

The flourometer 60 is of a conventional design and uses a light source to measure the light emissions from the monitoring fluid, fluorescent dye 26. For example, the fluorescent dye 26 has a light emission frequency which is outside the range of frequencies emitted by the diesel fuel 12 and the lubricating oil 18. The flourometer 60 excites the fluorescent dye 26 with a light source, not shown, and measures the light emitted from the fluorescent dye 26.

In this application, as shown in FIG. 3, a graph 80 displays an "X" axis representing time and a "Y" axis representing an intensity or density of the monitoring fluid, fluorescent dye 26. A preestablished line 82, shown as a solid line, represents an acceptable rate of contaminating fluid, diesel fuel 12 to operating fluid, lubricating oil 18 with the fluorescent dye 26 added to the diesel fuel 12. FIG. 3 also depicts a preestablished line 84, shown as a series of long dashes, represents an acceptable rate of contaminating fluid, diesel fuel 12 and operating fluid, lubricating oil 18 with the preestablished quantity of monitoring fluid, fluorescent dye 26 added to the lubricating oil 18.

In this application, as stated above, the distinguishing parameter (DP1, DP2, DP3) used is a light emission wave length. However, as an alternative a frequency could be used. For example, the contaminating fluid, diesel fuel 12 has a preestablished light emission length which falls within a range of about 3500 to 5500 angstroms. The operating fluid, lubricating oil 18 has a preestablished light emission wave length which falls within a range of about 3500 to 5500 angstroms and does not distinguish it from the light emission wave length of the contaminating fluid, diesel fuel 12. However, the monitoring fluid, fluorescent dye 26 has a preestablished light emission wave length which falls within a range of about 5500 to 9000 angstroms and does distinguish it from the light emission wave length of the contaminating fluid 12 and the operating fluid 18.

INDUSTRIAL APPLICABILITY

In one example of the operation of the method or monitoring system 10, the fuel tank 14 used with the engine 30 is filled with diesel fuel 12, contaminating fluid, near to its capacity, for example approximately 100 liters (about 53 gallons) and the oil pan 20 of the engine 30 is filled with lubricating oil 18, operating fluid, near to its capacity, for example approximately 30 liters (about 6 gallons). The predetermined quantity of the fluorescent dye 26, monitoring fluid in solid form, a powder, is added to the fuel tank 14 and mixes with the diesel fuel 12. In this application, the predetermined quantity of fluorescent dye 26 is for example, about 0.5 grams. The quantity of the fluorescent dye 26 can be varied without changing the gist of the invention. Prior to operation, the quantity of diesel fuel 14 and fluorescent dye 26, ratio or relationship is known or can be estimated and the quantity of fluorescent dye 26 in the lubricating oil 18, being none, is known. Thus, the line 82 in the graph 80 shown in FIG. 3 can be and is constructed.

The engine 30 is started and operated during normal operating cycles. As the piston 34 moves between the top position 42 and the bottom position 44 during the normal operating cycles, unburned fuel 12 and florescent dye 26 leaks past the seal member 38 and enters the oil pan 20. The diesel fuel 12 and florescent dye 26 mix with the lubricating oil 18. As time passes, the quantity of diesel fuel 14 and florescent dye 26 increase in the lubricating oil 18 during operation of the engine 30, the flourometer 60 determines the quantity of florescent dye 26 in the lubricating oil 18 by monitoring the intensity or density of the particles having the wave length of about 5670 angstroms, the wave length of the monitoring fluid 26. The flourometer 60 monitors the quantity of florescent dye 26 in the lubricating oil 18 and conveys the quantity to the computer 24. The computer 24 compares the preestablished distinguishing parameter (DP1, DP2, DP3) quantity of florescent dye 26 with time, and defines the actual dilution of the lubricating oil 18. The actual dilution is plotted as time passes and compared with the preestablished line 82. Thus, an actual dilution rate verses an acceptable or desired rate can be compared. If the actual dilution rate is worse than the desired rate the engine 30 can be shut down and repaired prior to a major failure. This allows the engine 30 maintenance to be scheduled verse a failure resulting in unpredicted down time.

In another example, the fuel tank 14 is filled with diesel fuel 12, contaminating fluid, near to its capacity, for example approximately 100 liters (about 53 gallons) and the oil pan 20 of the engine 30 is filled with lubricating oil 18, operating fluid, near to its capacity, for example approximately 30 liters (about 6 gallons). The predetermined quantity of the fluorescent dye 26, monitoring fluid in solid form, a powder, is added to the oil pan 20 and mixes with the lubricating oil 18. In this application, the predetermined quantity of fluorescent dye 26 is for example, about 0.17 grams. Prior to operation, the quantity of lubricating oil 18 and fluorescent dye 26, ratio or relationship is known or can be estimated. Thus, the line 84 in the graph 80 shown in FIG. 3 can and is constructed.

The engine 30 is started and operated during normal operating cycles. As the piston 34 moves between the top position 42 and the bottom position 44 during the normal operating cycles, unburned fuel 12 leaks past the seal member 38 and enters the oil pan 20. The diesel fuel 12 mixes with the lubricating oil 18 and increases the relationship or ratio of mixed diesel fuel 12 and lubricating oil 18 decreasing the ratio of florescent dye, monitoring fluid 26 to the total quantity of diesel fuel, contaminating fluid 12 and operating fluid, lubricating oil 18. As time passes, the quantity of florescent dye 26 decreases in comparison to the quantity of diesel fuel 12 mixed with the lubricating oil 18 during operation of the engine 30. The flourometer 60 determines the quantity of florescent dye 26 in the mixture of diesel fuel 12 and the lubricating oil 18 by monitoring the intensity or density of the particles having the wave length of about 5670 angstroms or in this application over 5500 angstroms, the wave length of the monitoring fluid, florescent dye 26 above that of either the diesel fuel 12 or the lubricating oil 18. The flourometer 60 monitors the quantity of florescent dye 26 in the mixture of diesel fuel 12 and the lubricating oil 18 and the quantity of the mixture diesel fuel 12 and the lubricating oil 18 and conveys the quantities to the computer 24. The computer 24 compares the preestablished distinguishing parameter (DP1, DP2, DP3), quantity of florescent dye 26 to the mixture of diesel fuel 12 and lubricating oil 18 with time, and defines the actual dilution of the lubricating oil 18. The actual dilution is plotted as time passes and compared with the preestablished line 84. Thus, an actual dilution rate verses an acceptable or desired rate can be compared. If the actual dilution rate is worse than the desired rate the engine 30 can be shut down and repaired prior to a major failure. This allows the engine 30 maintenance to be scheduled versus a failure resulting in unpredicted down time.

What is claimed is:

1. A system for monitoring a dilution of a first fluid into a commodity of said system; said system comprising:
    said commodity having a preestablished distinguishing parameter (DP2);
    a first fluid supply reservoir having said first fluid therein, said first fluid having a preestablished distinguishing parameter (DP1) being different from said preestablished distinguishing parameter (DP2) of said commodity;
    a monitoring fluid having a preestablished distinguishing parameter (DP3) being different from said preestablished distinguishing parameter (DP2) of said commodity and said preestablished distinguishing parameter (DP1) of said first fluid, wherein at least one of commodity preestablished distinguishing parameter (DP2), first fluid preestablished distinguishing parameter (DP1), and monitoring fluid preestablished distinguishing parameter (DP3) is a light emission parameter;
    an apparatus having at least one of a plurality of components making up said apparatus, said apparatus being operated in a preestablished cycle; and
    a monitoring station having at least one of a display monitor and a recording device, said monitoring station having a device having the capability to distinguish at least two of said preestablished distinguishing parameter (DP3) of said monitoring fluid from said preestablished distinguishing parameter (DP2) of said commodity and said preestablished distinguishing parameter (DP1) of said first fluid.

2. The monitoring system of claim 1, wherein said light emission parameter is a wavelength.

3. The monitoring system of claim 1, wherein said commodity being in one of a solid, liquid or gaseous state.

4. The monitoring system of claim 1, wherein said first fluid being in one of a solid, liquid, or gaseous state.

5. The monitoring system of claim 1, wherein said monitoring fluid being in one of a solid, liquid, or gaseous state.

6. A system for monitoring a dilution of a first fluid into a second fluid of an apparatus, said apparatus having a plurality of components and at least one of said components being movable relative to another one of said components during a cycle of said apparatus; said system for monitoring a dilution comprising:
   a first fluid having a preestablished distinguishing parameter (DP1) and being stored in a first fluid storage reservoir;
   a second fluid having a preestablished distinguishing parameter (DP2) being different from said preestablished distinguishing parameter (DP1) of said first fluid and being stored in a second fluid storage reservoir, said first fluid storage reservoir being separated from said second fluid storage reservoir;
   a monitoring fluid being stored in one of said first fluid storage reservoir or said second fluid storage reservoir, said monitoring fluid having a preestablished distinguishing parameter (DP3) being different from said preestablished distinguishing parameter (DP1) of said first fluid and said preestablished distinguishing parameter (DP2) of said second fluid, wherein at least one of second fluid preestablished distinguishing parameter (DP2), first fluid preestablished distinguishing parameter (DP1), and monitoring fluid preestablished distinguishing parameter (DP3) is a light emission parameter; and
   a monitoring station.

7. The system of claim 6, wherein said monitoring fluid being stored in said first fluid storage reservoir.

8. The system of claim 7, wherein said monitoring station having a device therein distinguishing said preestablished distinguishing parameter (DP1) of said first fluid from said preestablished distinguishing parameter (DP1) of said second fluid.

9. The system of claim 8, wherein said monitoring station has at least one of a display monitoring device and a recording device therein.

10. The system of claim 8, wherein said monitoring station has each of a display monitoring device and a recording device.

11. The system of claim 6, wherein said monitoring fluid being a fluorescent dye.

12. The system of claim 11, wherein each of said preestablished distinguishing parameter (DP3) of said monitoring fluid, said preestablished distinguishing parameter (DP1) of said first fluid and said preestablished distinguishing parameter (DP2) of said second fluid being a measurement of an emission from said fluorescent dye.

13. The system of claim 12, wherein said fluorescent dye has a predetermined frequency of emitting a light being outside a range of frequency of emitting said light of said second fluid.

14. The system of claim 12, wherein said fluorescent dye has a predetermined frequency of emitting a light being outside a range of frequency of emitting said light of said first fluid and said second fluid.

15. A method of monitoring a diluting of a commodity, said method comprising:
   having a commodity storage reservoir having a commodity therein, said commodity having a predetermined distinguishing parameter (DP2);
   having a first fluid storage reservoir having a first fluid therein, said first fluid having a predetermined distinguishing parameter (DP1) being different from said predetermined distinguishing parameter (DP2) of said commodity wherein at least one of commodity predetermined distinguishing parameter (DP2) and first fluid predetermined distinguishing parameter (DP1) is a light emission parameter;
   having an apparatus being connected to said first fluid storage reservoir and being connected to said commodity; and
   having a monitoring station being in operational communication with said commodity, said monitoring station having a device therein distinguishing between one of said pre determined distinguishing parameter (DP1) of said first fluid and said predetermined distinguishing parameter (DP2) of said commodity.

16. The method of claim 15 including a monitoring fluid having a predetermined distinguishing parameter (DP3) being different from said predetermined distinguishing parameter (DP2) of said commodity.

17. The method of claim 16, wherein said predetermined distinguishing parameter (DP3) of said monitoring fluid being different from said predetermined distinguishing parameter (DP1) of said first fluid.

18. The method of claim 17, wherein said predetermine distinguishing parameter (DP3) of said monitoring fluid being a measurement of light emitted from said monitoring fluid.

19. The method of claim 18, wherein said monitoring fluid being a fluorescent dye.

20. The method of claim 15, wherein said monitoring station having at least one of a display monitor and a recording device.

* * * * *